US012589332B2

(12) United States Patent
Wu

(10) Patent No.: US 12,589,332 B2
(45) Date of Patent: Mar. 31, 2026

(54) LIQUID SEPARATION KIT

(71) Applicant: Fu Jen Catholic University, New Taipei City (TW)

(72) Inventor: Yi-No Wu, New Taipei City (TW)

(73) Assignee: FU JEN CATHOLIC UNIVERSITY, New Taipei City (TW)

( * ) Notice: Subject to any disclaimer, the term of this patent is extended or adjusted under 35 U.S.C. 154(b) by 508 days.

(21) Appl. No.: 18/013,816

(22) PCT Filed: Nov. 23, 2020

(86) PCT No.: PCT/CN2020/130737
    § 371 (c)(1),
    (2) Date: Dec. 29, 2022

(87) PCT Pub. No.: WO2022/068023
    PCT Pub. Date: Apr. 7, 2022

(65) Prior Publication Data
    US 2023/0285875 A1      Sep. 14, 2023

(30) Foreign Application Priority Data

Sep. 29, 2020    (CN) .......................... 202011050719.8

(51) Int. Cl.
    *B01D 17/00*      (2006.01)
    *A61J 1/05*       (2006.01)
    *A61M 1/02*       (2006.01)
    *B01L 3/00*       (2006.01)

(52) U.S. Cl.
    CPC ................ *B01D 17/00* (2013.01); *A61J 1/05* (2013.01); *A61M 1/029* (2013.01); *B01L 3/50273* (2013.01); *B01L 2400/0478* (2013.01)

(58) Field of Classification Search
    CPC ........ B01D 17/00; A61J 1/05; B01L 3/50273; B01L 2400/0478; A61M 1/029
    See application file for complete search history.

(56) References Cited

FOREIGN PATENT DOCUMENTS

| | | |
|---|---|---|
| CN | 102947009 A | 2/2013 |
| CN | 107771079 A | 3/2018 |
| CN | 208990300 U | 6/2019 |
| CN | 110856775 A | 3/2020 |
| CN | 211383916 U | 9/2020 |
| EP | 1566191 A2 | 8/2005 |
| KR | 101928515 B1 * | 12/2018 |
| WO | WO-2015070273 A1 | 5/2015 |

OTHER PUBLICATIONS

Machine translation of KR 10-1928515.*

* cited by examiner

*Primary Examiner* — Benjamin L Lebron
(74) *Attorney, Agent, or Firm* — MUNCY, GEISSLER, OLDS & LOWE, P.C.

(57) ABSTRACT

The present invention provides a liquids separation kit that has a control unit on a container body to selectively control the separation or conduction between a first room and outside the container body and between the first room and a second room, thereby easily obtaining a first component which is perhaps highly concentrated after separation process.

13 Claims, 9 Drawing Sheets

10

10'

LIQUID SEPARATION KIT

CROSS REFERENCE TO RELATED APPLICATIONS

This application is a national stage application of International Patent Application No. PCT/CN2020/130737, filed on Nov. 23, 2020, which claims priority to China Patent Application No. 202011050719.8, filed on Sep. 29, 2020, the contents of which are incorporated herein by reference in their entirety.

FIELD OF THE INVENTION

The present invention relates to techniques of liquids sampling and separation, specifically to a liquids separation device that incorporates liquids sampling and multiple separation processes.

BACKGROUND OF THE INVENTION

When conducting certain researches, experiments and clinical trials, there is always a need for obtaining certain components from a liquid sample with certain concentration. Conventionally, there are different tools utilized in different steps such as suctioning, separating, removing and storage during the process. However, with all the different tools utilized in the process, there is possibility of the liquid samples being contaminated and consequently tampering with, for example, the purity or concentration rate of the target components, thereby the final results.

Take the platelet-rich plasma (PRP) for example. PRP is the concentrated platelets with some other constituents of blood, prepared by utilizing separation kits to perform the separation process with constant speed centrifugation based on the different sedimentation coefficients of the constituents in the whole blood sample. Since the PRP is from the patient himself, the treatment with PRP is quite safe. As the blood samples can be easily obtained and allergy reactions or rejections would hardly be triggered, PRP treatment is significantly performed in treating osteoarthritis, joint pain (shoulders, hips, knees and ankles), muscle strains, tendinopathy injuries, soft tissue injuries, bone fracture healing improvement, and so on.

The separation kits used by the medical staff usually include at least two tools, the collecting tool and the separating tool. A syringe, functioning as the collecting tool, is utilized to collect the blood sample from the patients and then inject the sample into a test tube, functioning as the separating tool. After the centrifugation by a separation machine (or known as centrifuge machine), the PRP can be obtained. The centrifugation process includes many detailed works and is rather complicated, and the different concentration rate of the PRP obtained will increase the difficulty in clinical use. Also, it requires various tools for the entire separation process. The risk of contaminating the blood samples is therefore increased.

Patent application No. CN 201680036560.X disclosed a dual-syringe structure that is able to directly obtain the PRP without opening the structure. Although the PRP can be obtained without opening the dual-syringe structure, such structure, in fact, still includes two tools and utilizes different syringes as first syringe and the second syringe in different steps in the process. During the separation process, it still needs different tools for holding the constituents and for separation, same as in the conventional way. The dual-syringe structure may be able to reduce the risk of human operation errors and contamination; however, when it comes to a great amount of blood samples, there is no guarantee in the operators being able to keep the blood samples clean with the multiple inserting or engaging between the tools and the separation step. There is a risk of misplacing the samples due to the need for regularly exchanging the tools in the entire process. In a minor situation, there may be minor side effects with a small dosage; in a major situation, there may be rejections that cause urgent threats to the subjects due to low compatibility.

Therefore, the present invention provides a liquids separation kit that resolves the deficiencies in the prior art.

SUMMARY OF THE INVENTION

A first objective of the present invention is to provide a liquids separation kit that achieves a process from collecting the whole blood samples to separating the components in the blood in the same container body, so as to ensure no blood contamination.

A second objective of the present invention is to have the liquids separation kit perform at least two separation process to obtain a component in the blood, e.g., the platelets, the blood plasma, the red blood cells, with high concentration.

A third objective of the present invention is to have the liquids separation kit to be able to obtain and prepare a component with high concentration.

To achieve the objectives mentioned above, the liquids separation kit of the present invention is able to simultaneously hold a first component and a second component separated from a liquid after separation process. The liquids separation kit includes a container body, a connecting piece, a control module and a piston. The container body includes a first room and a second room, both having a free end and a connecting end; wherein the first room holds the liquid or the first component and the second room holds the second component. The connecting piece has a first end and a second end. The first end is connecting to the connecting end of the first room; wherein partial of the connecting piece is exposed in between the first and second rooms, or wherein partial of the connecting piece is arranged outside the second room and the second end thereof is extending towards the free end of the second room, or wherein the connecting piece is arranged inside the second room and has the second end thereof extending towards the free end of the second room, rendering the second end thereof being arranged inside the second room. The control module includes a plurality of tubes and a control unit. The control unit is coupled to the tubes for conducting or stopping liquids flows within the tubes by operating the control unit. The tubes are individually connecting to the second end, the second room or the free end of the second room. The piston is disposed in the first room and is movable therein, so as to produce a suction force or a pressing force at the connecting end of the first room.

In an embodiment, the liquids separation kit further includes a top cap arranged at the free end of the first room for confining the piston to being inside the first room.

In an embodiment, the control unit thereof is operated and enables the second end and the free end of the second room to be conducting, and when the piston is moving from the connecting end of the first room towards the free end of the first room, the liquid is sucked into the first room from the free end of the second room.

In an embodiment, the control unit thereof is operated and enables the second end and the second room to be conducting, and when the piston is moving from the free end of the first room towards the connecting end of the first room, the second component is pushed into the second room from the first room.

In an embodiment, the control unit thereof is operated and enables the second end and the free end of the second room to be conducting, thereby the first component is pushed to the free end of the second room from the first room when the piston is moving from the free end of the first room towards the connecting end of the first room.

In an embodiment, the piston thereof moves via traction and pressing of an external force to change its position within the first room.

In an embodiment, the liquids separation kit further includes a threaded rod connecting to the piston and being driven by the external force to change the position of the piston within the first room.

In an embodiment, the liquids separation kit further includes a bottom cap engaging the free end of the second room, in order to prevent the free end of the second room from being connecting to outside the container body.

In an embodiment, the second room thereof further forms an observation section to expose the second end for observation of at least one of the liquid at the second end, the first component and the second component.

In an embodiment, the observation section is formed by at least a block or a blocking element.

In comparison with the conventional technologies, the present invention provides a liquids separation kit that is able to perform multiple (for example, twice) separation process with centrifuging, vibrating, shaking, depositing . . . , etc., and obtain a first component, a second component, and so on. Also, the present invention provides the container body for blood sampling, separating and storage altogether, preventing the liquids from potential contamination while being transported or exchanged between different containers.

In an embodiment, the liquid is the blood for exemplary purpose, and the liquids separation kit can collect the whole blood samples from the subjects, the blood bags or blood drawing devices (such as syringes). And after a first centrifuge process, the red blood cells, platelets and other components in the blood can be separated therefrom; then a second centrifuge process can be performed to the platelets and other components to obtain highly concentrated platelets.

DETAILED DESCRIPTION OF THE PREFERRED EMBODIMENTS

In order to fully comprehend the objectives, features and efficacy of the present invention, a detailed description is described by the following substantial embodiments in conjunction with the accompanying drawings. The description is as below.

The description of unit, element and component in the present invention uses "one", "a", or "an". The way mentioned above is for convenience, and for general meaning of the category of the present invention. Therefore, the description should be understood as "include one", "at least one", and include the singular and plural forms at the same time unless obvious meaning.

The description of comprise, have, include, contain, or another similar semantics has the non-exclusive meaning. For example, an element, structure, product, or device contain multi requirements are not limited in the list of the content, but include another inherent requirement of element, structure, product or device not explicitly listed in the content. In addition, the term "or" has an inclusive meaning instead of an exclusive one.

Figure 1:
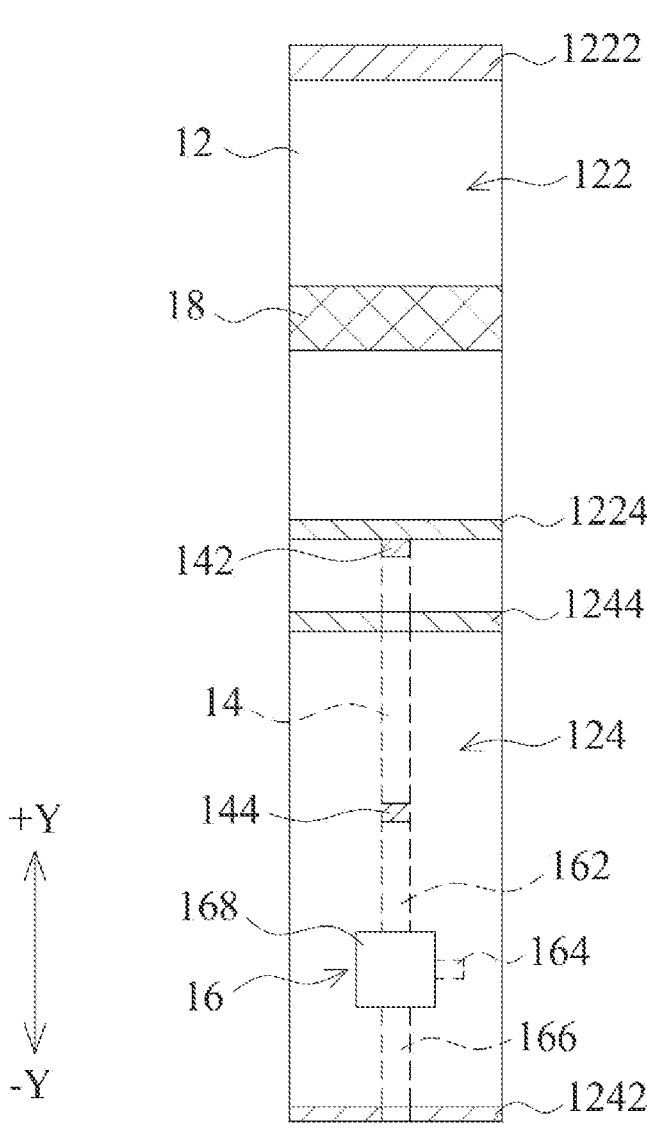
FIG. 1 is a sectional view of the present invention, a liquids separation kit, in a first embodiment.

Referring to FIG. 1, a sectional view of the present invention—a liquids separation kit—in the first embodiment is illustrated. As shown in FIG. 1, the liquids separation kit 10 is able to simultaneously hold a first component 4 (see FIGS. 8, 9A and 9B) and a second component 6 (see FIGS. 8, 9A and 9B) separated from a liquid 2 after separation process (see FIGS. 7A and 7B). Herein, the Platelet-rich Plasma (PRP) separated from the whole blood is taken for exemplary illustrations. In other embodiments, any solvent in liquid form that requires component separation is applicable. Also, the whole blood herein is human blood. Human blood consists of blood plasma and blood cells, in which the blood plasma has a volume of 55% whereas the blood cells is 45%. The blood plasma has a light amber color and consists of 90% water and 7-8% plasma protein, and the rest constituents are nutrients, wastes, gas substances, and so on. There are many different kinds of proteins in the blood plasma, such as antibodies, hormones and enzymes, each having a significant function. The blood cells can be mainly divided into red blood cells, white blood cells and platelets, each has its own function such as transporting the gas substances, defense for diseases and blood coagulation.

Additionally, when the medical staff (also known as the users) is utilizing the present invention described herein, they can also perform the separation process on the whole blood by means of conventional centrifuges or other external forces such as centrifugal force and shaking force.

The liquids separation kit 10 includes a container body 12, a connecting piece 14, a control module 16 and a piston 18.

The container body 12 forms a first room 122 and a second room 124. Herein, the container body 12 is in a cylindrical shape which is similar to common test tubes in the laboratories; but the present invention is not limited to such shape. Any skilled person in this art can have it shaped as suitable for practical applications.

The first room 122 forms a free end 1222 and a connecting end 1224; wherein the first room 122 holds the liquid 2 or the first component 4. In this embodiment, the first component 4 is majorly platelets, blood plasma, and so on.

The second room 124 forms a free end 1242 and a connecting end 1244; wherein the second room 124 holds the second component 6. In this embodiment, the second component 6 is majorly red blood cells.

The connecting piece 14 has a first end 142 and a second end 144. The first end 142 is connecting to the connecting end 1224 of the first room 122. There are several arrangements among the connecting piece 14, the first room 122 and the second room 124. Examples are described in the following embodiments.

Pattern 1 is illustrated as the first embodiment shown in FIG. 1.

In Pattern 1, the liquids separation kit 10 has partial of the connecting piece 14 exposed in between the first and second rooms 122, 124; the rest of the connecting piece 14 can be arranged inside or outside the second room 124. Herein, the rest of the connecting piece 14 is arranged inside the second room 124 for exemplary purpose.

Figure 2:
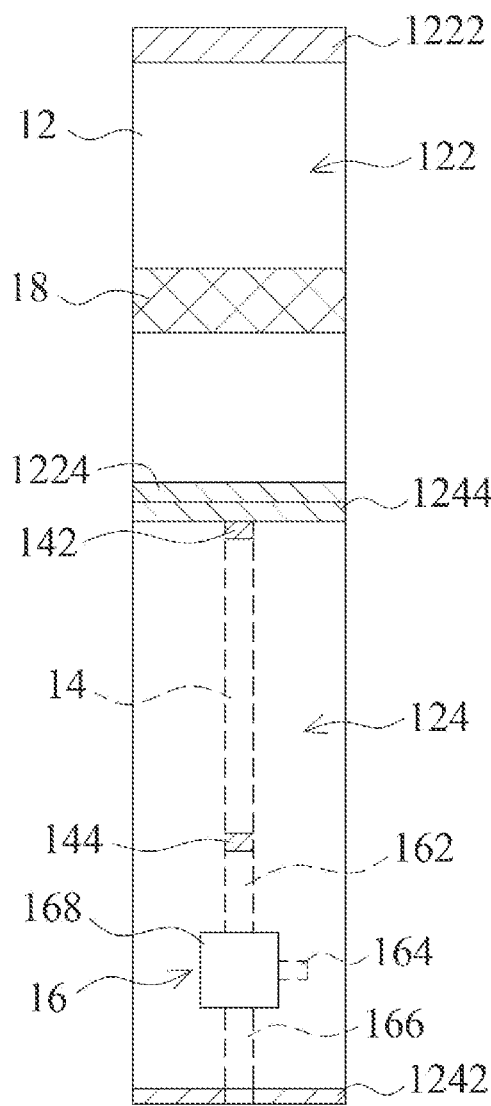
FIG. 2 is a sectional view of the present invention, the liquids separation kit, in a second embodiment.

Pattern 2 is in reference to FIG. 2, a sectional view of the present invention in the second embodiment.

In Pattern 2, the liquids separation kit 10' has the connecting piece 14 thereof arranged inside the second room 124 and has the second end 144 thereof extending towards the free end 1242 of the second room 124, rendering the second end 144 being arranged inside the second room 124.

Figure 3:
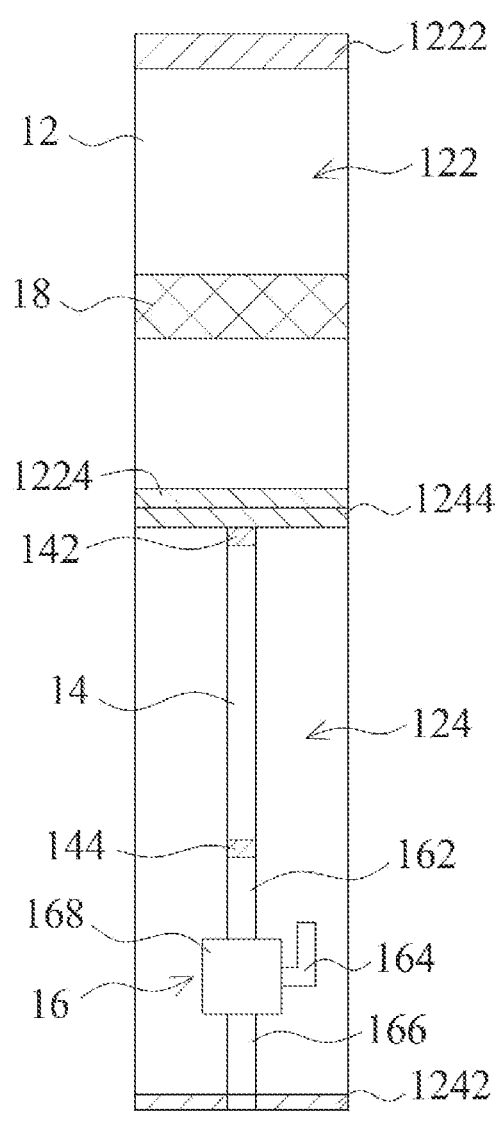
FIG. 3 is a sectional view of the present invention, the liquids separation kit, in a third embodiment.

Pattern 3 is in reference to FIG. 3, a sectional view of the present invention in the third embodiment.

In Pattern 3, the liquids separation kit 10" has partial of the connecting piece 14 arranged outside the second room 124 and has the second end 144 extending towards the free end 1242 of the second room 124.

Referring back to FIG. 1, the control module 16 includes three tubes 162, 164, 166 and a control unit 168. In other embodiments, the amount of the tubes is not limited to three; it can be more than or less than three. The control unit 168 is coupled to the tubes. The control unit 168 can be, for example, a valve for regulating the liquids flows within the tubes 162, 164, 166. By operating the control unit 168, the liquids flows within the tubes 162, 164, 166 can be conducted or stopped. The operation of the control unit 168 to regulate the liquids flows can be performed by means of knob switches, press buttons, pushing rods, and so on. In addition, the materials for the tubes 162, 164, 166 can be plastics, silicones, and so on; and the hardness of the tubes 162, 164, 166 can also be decided individually without any limitations. In this embodiment, one of the tube 162 is connecting to the second end 144; another tube 164 is connecting to the second room 124 and the other tube 166 is connecting to the free end 1242 of the second room 124.

The piston 18 is disposed in the first room 122. By moving the piston 18 within the first room 122, a suction force or a pressing force can be produced at the connecting end 1224 of the first room 122. For instance, when the piston 18 is moving towards a +Y direction, it creates a suction force at the connecting end 1224 of the first room 122; on the contrary, when it is moving towards a −Y direction, it creates a pressing force at the connecting end 1224 of the first room 122. The moving of the piston 18 within the first room 122 described here can be operated by an external force via traction or pressing, such as vacuum force, magnetic force, pull force, pressing force and torque. One of the aforesaid forces will be illustrated herein as the embodiment, but the present invention is not limited to any of the operation described above. Any operation that moves the piston 18 within the first room 122 is included within the scope of the present invention.

Since the connecting end 1224 of the first room 122 is connecting the first end 142 of the connecting piece 14, the suction force or pressing force created at the first end 1224 will also have effects on the second end 144 of the connecting piece 14 and further on the tube 162. By operating the control unit 168, the tube 164 or 166 would also has the suction force or pressing force therein. In other words, the suction force or pressing force described here can decide the movements of the blood, the blood plasma or the blood cells within the first room 122, the connecting piece 14 and the first room 122 by operating the control unit 168.

Figure 4:
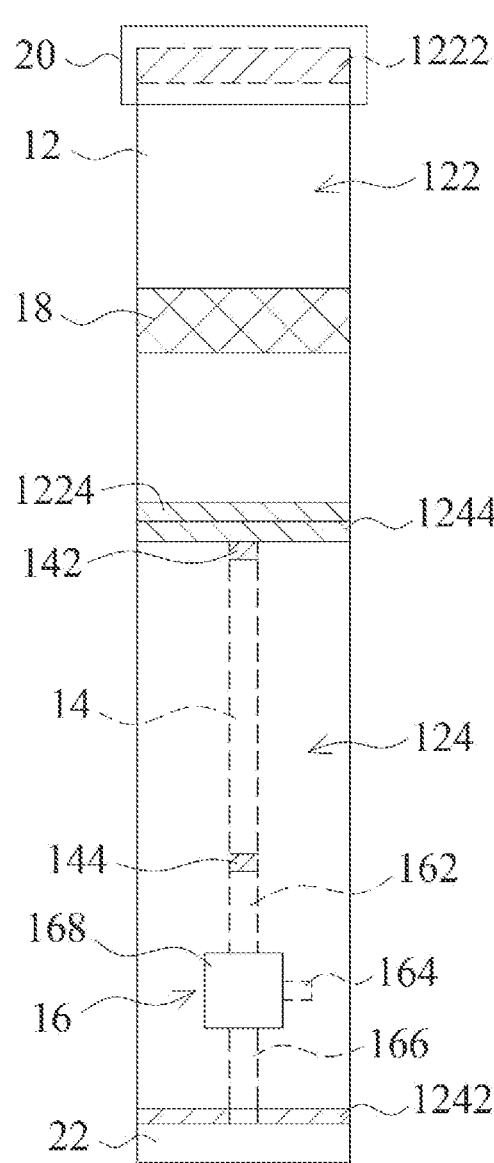
FIG. 4 is a sectional view of the present invention, the liquids separation kit, in a fourth embodiment.

Referring to FIG. 4, a sectional view of the present invention in the fourth embodiment, the liquids separation kit 10 further includes a top cap 20 and a bottom cap 22 in addition to the container body 12, the connecting piece 14, the control module 16 and the piston 18 as described in the first embodiment. In this embodiment, the liquids separation kit 10 can hold the first component 4 and the second component 6 of the liquid 2 for further separation process and carrying around.

The container body 12, the connecting piece 14, the control module 16 and the piston 18 are as described above.

The top cap 20 is arranged at the free end 1222 of the first room 122 for confining the piston 18 to being inside or sealing the first room 122.

The bottom cap 22 is engaging the free end 1242 of the second room 124 in order to prevent the free end 1242 from being connecting to outside the container body 12.

Figure 5:
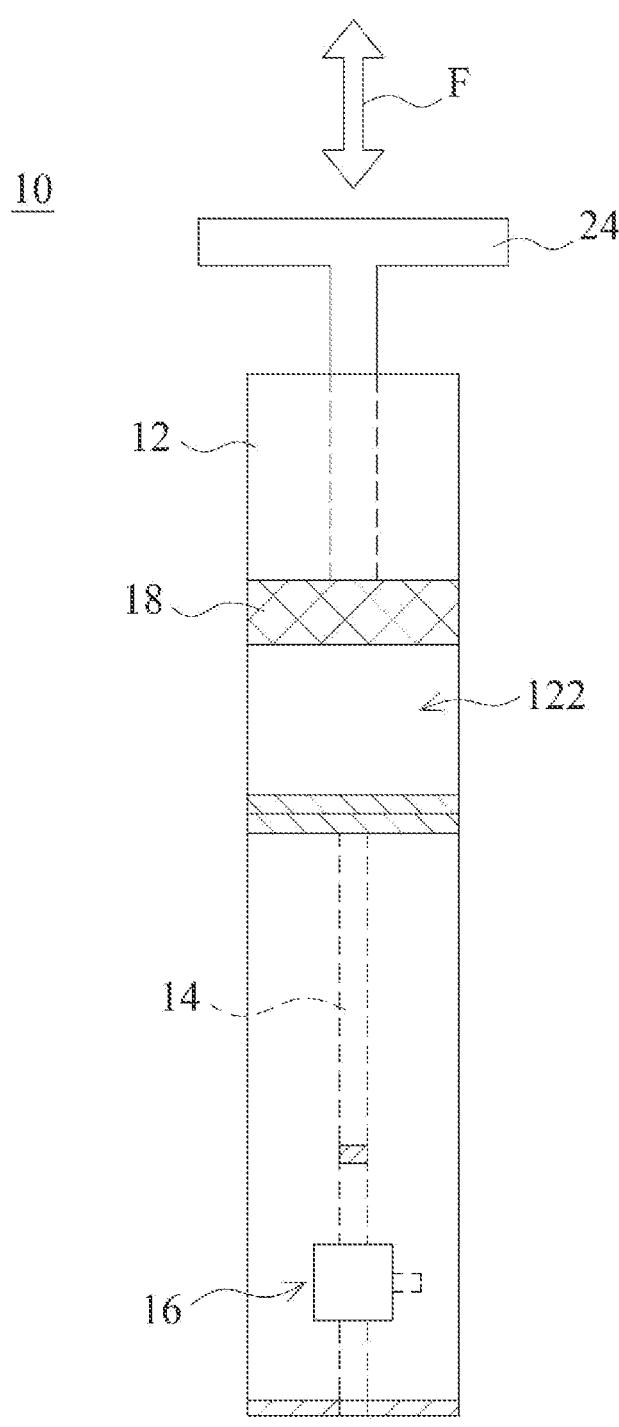
FIG. 5 is a sectional view of the present invention, the liquids separation kit, in a fifth embodiment.

Referring to FIG. 5, a sectional view of the present invention in the fifth embodiment, the liquids separation kit 10 further includes a threaded rod 24 in addition to the container body 12, the connecting piece 14, the control module 16 and the piston 18 as described in the first embodiment.

The container body 12, the connecting piece 14, the control module 16 and the piston 18 are as described above.

The threaded rod 24 is engaging the piston 18 and driven by an external force F to change the position of the piston 18 within the first room 122. Wherein the way threaded rod 24 is engaging the piston 18 can be, for instance, forming an internal threads on partial of the piston 18 for screwing and engaging an external threads at an end of the threaded rod 24. By having the external threads screwed into the internal threads, the threaded rod 24 and the piston 18 are fixedly engaged and the external force F is able to have effect on the threaded rod 24 moving along the +Y or −Y direction, thereby changing the position of the piston 18 within the first room 122. In this embodiment, the internal threads can be formed as a screw sleeve (not shown) arranged at the end of the threaded rod 24, and the external threads can be formed on a protruding block (not shown) arranged on the piston 18.

What is worth mentioning is that the threaded rod 24 is only illustrated in one of the embodiments for changing the position of the piston 18 within the first room 122; in other embodiments, the external force F can also be created by other traction or pressing mechanism.

Figure 6:
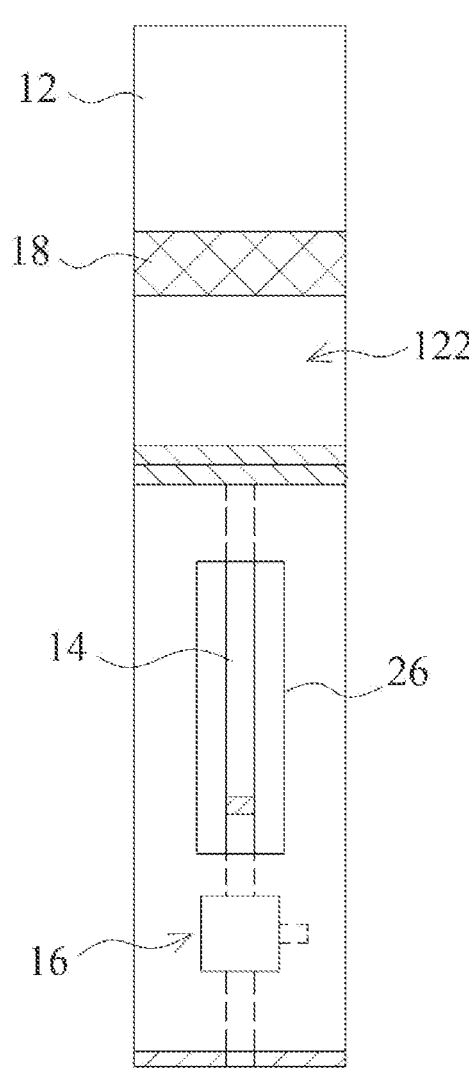
FIG. 6 is a sectional view of the present invention, the liquids separation kit, in a sixth embodiment.

Referring to FIG. 6, a sectional view of the present invention in the sixth embodiment, the liquids separation kit 10 further includes an observation section 26 formed at the second room 124, in addition to the container body 12, the connecting piece 14, the control module 16 and the piston 18 as described in the first embodiment.

The container body 12, the connecting piece 14, the control module 16 and the piston 18 are as described above.

The observation section 26 is mainly for exposing the connecting piece 14 for observation of the liquid 2 therein, the first component 4 and the second component 6. In this embodiment, the connecting piece 14 is arranged at the second room 124 (with reference to FIG. 1). If the second component 6 is the red blood cells, it may cover the connecting piece 14 and obstructs the observation or operation. Therefore, the observation section 26 can be formed by, for example, having blocks (not shown), blocking elements (not shown) or protruding elements (not shown) connecting the connecting piece 14 and an inner periphery of the second room 124. With the red blood cells being blocked, the transparent blocks on the container body 12 near the second room 124 can form the observation section 26.

What is worth mentioning is that the observation section 26 can be formed in any other way or element and is not limited to such application.

On the other hand, if it is as in the third embodiment, with the connecting piece 14 exposed outside the second room 124, there is no need to form the observation section 26 since the second component 6 will not cover anything.

FIGS. 7A, 7B, 8, 9A and 9B illustrated the operation of the present invention in the embodiments.

Figure 7A:
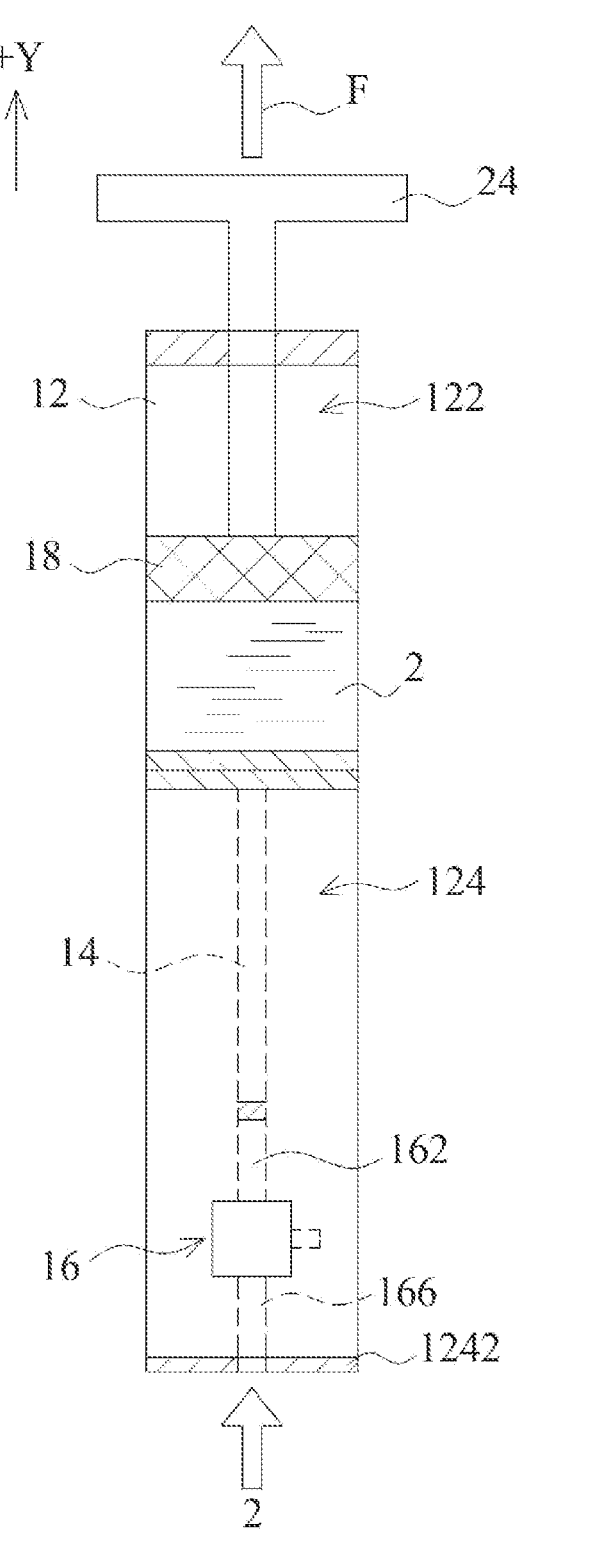
FIG. 7A is a schematic diagram of the present invention, illustrating a blood sampling process according to the embodiments.

In FIG. 7A, a schematic diagram illustrating the liquids separation kit 10 collecting the blood sample, the control module 16 of the liquids separation kit 10 is operated to conduct the tubes 162, 166. The threaded rod 24 is engaging the piston 18 and moves along the +Y direction via the external force F, thereby creating a suction force at the free end 1242 of the second room 124 to collect the liquid 2 from human body or a container (not shown) stored with the liquid 2. The container can be a blood bag, a test tube, and so on, and the liquid 2 is stored in the first room 122.

Figure 7B:
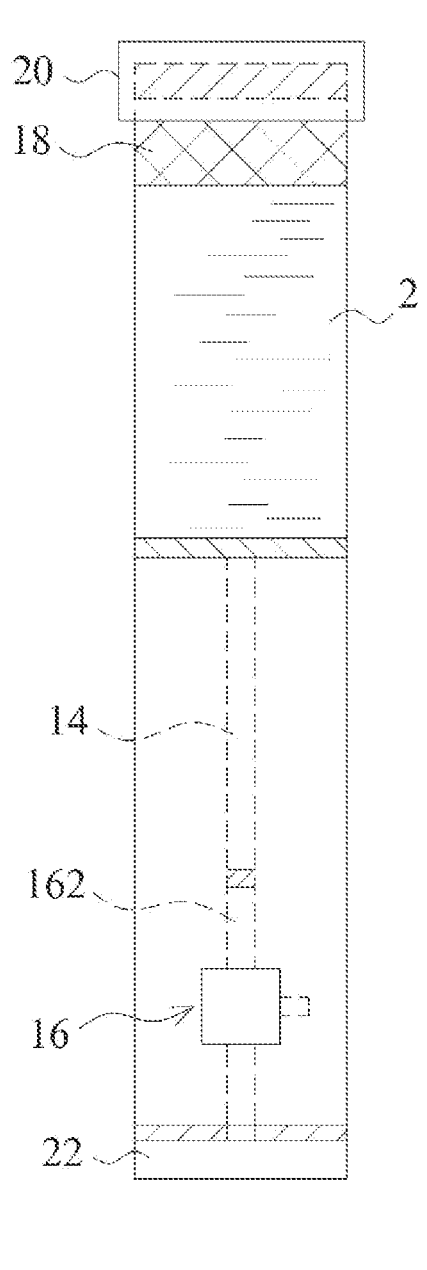
FIG. 7B is a schematic diagram of the present invention, illustrating a status thereof when the blood sample is being transported and in a separation process according to the embodiments.

In FIG. 7B, a schematic diagram illustrating the status of the liquids separation kit 10 when the blood sample is being transported and in a separation process, the control module 16 of the liquids separation kit 10 is operated to block the tube 162 from conducting through to other tubes and the threaded rod 24 is disengaged therefrom; the top cap 20 is arranged at the free end 1222 (with reference to FIG. 1) of the first room 122 (with reference to FIG. 7A) and the bottom cap 22 is arranged at the free end 1242 (with reference to FIG. 7A) of the second room 124 (with reference to FIG. 7A). The liquid 2 is thereby stored in the first room 122.

Figure 8:
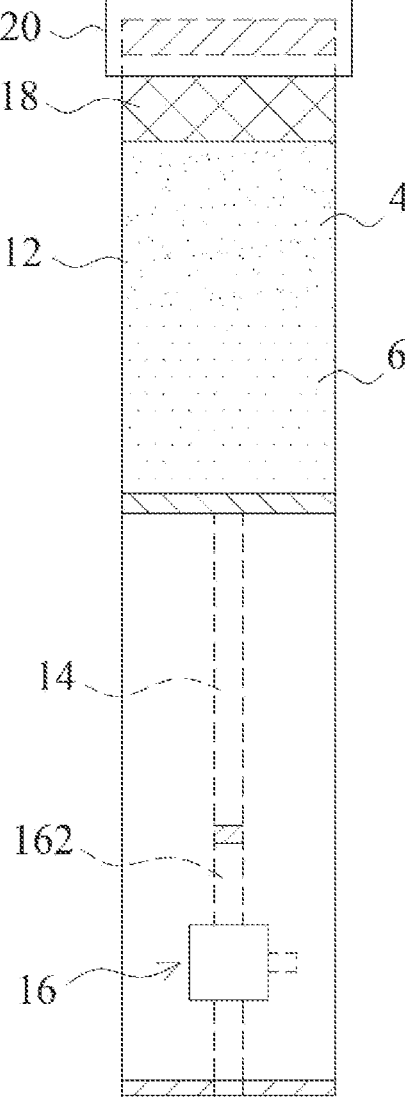
FIG. 8 is a schematic diagram of the present invention, illustrating a status thereof after a centrifuge process, according to the embodiments.

In FIG. 8, a schematic diagram illustrating the status of the liquids separating kit 10 after a centrifuge process, the liquid 2 in the first room 122 (with reference to FIG. 1) is separated and the first component 4 and the second component 6 are obtained after the first centrifuge process by, for example, a centrifuge machine (not shown). The first component 4 can be the platelets and other constituents, and the second component 6 can be the red blood cells.

Figure 9A:
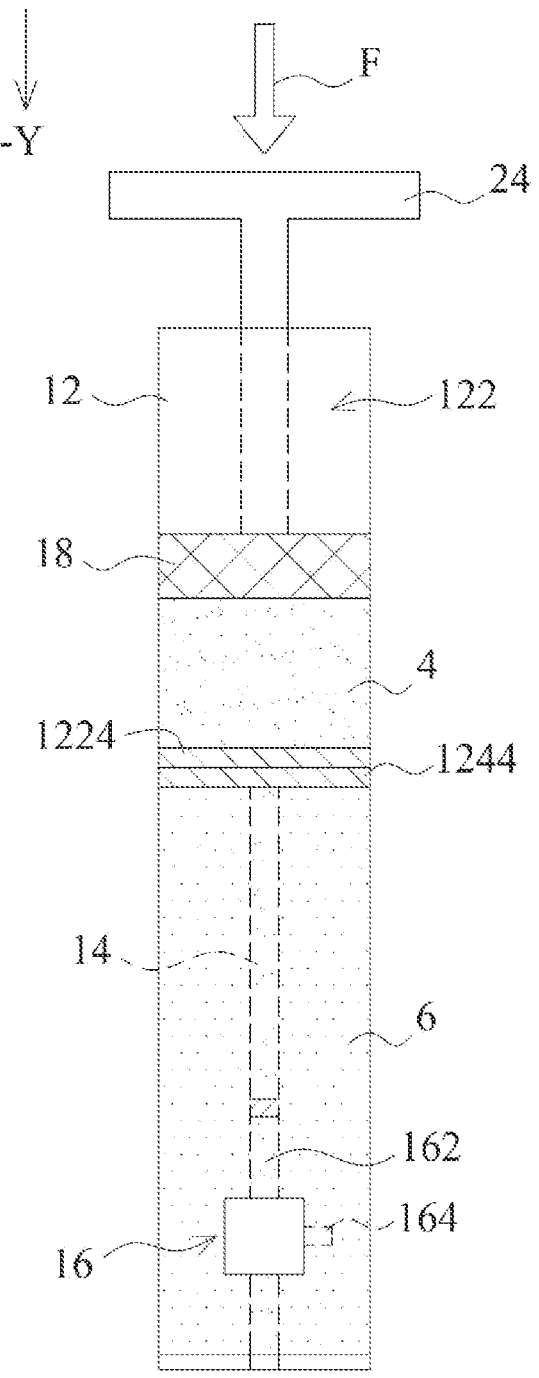
FIG. 9A is a schematic diagram of the present invention, illustrating a first separation process according to the embodiments.

In FIG. 9A, a schematic diagram illustrating a status of the liquids separation kit 10 in the first separation process, the control module 16 thereof is operated to conduct the tubes 162, 164 and the threaded rod 24 is engaging the piston 18 and moves along the —Y direction via the external force F, thereby the first and second components 4, 6 are pushed into the connecting piece 14 via the connecting end 1224 of the first room 122. Herein, the second component 6 enters into the connecting piece 14 first and then to the second room 124 via the tube 164 (with reference to FIG. 1). In this embodiment, when observing the second component 6 is completely or almost entirely in the second room 124, the external force F is stopped. In other words, the second component 6 is mainly stored in the second room 124; there is very little to none of the second component 6 in the connecting piece 14 or the first room 122.

Figure 9B:
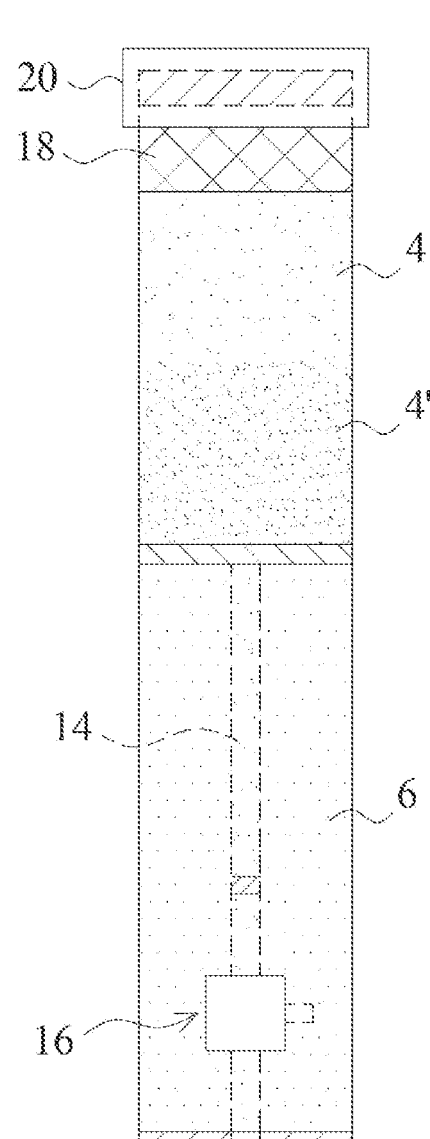
FIG. 9B is a schematic diagram of the present invention, illustrating a status thereof when the blood sample is being transported and in another separation process according to the embodiments.

In FIG. 9B, a schematic diagram illustrating the status of the liquids separation kit 10 when the blood sample is being transported and in another separation process, the control module 16 thereof is operated again to block the tube 162 (with reference to FIG. 9A) from conducting through to other tubes and the threaded rod 24 is disengaged therefrom; the top cap 20 is arranged at the free end 1222 (with reference to FIG. 1) of the first room 122 (with reference to FIG. 1) and the bottom cap 22 is arranged at the free end 1242 (with reference to FIG. 1) of the second room 124 (with reference to FIG. 1). After the second separation process performed by, for example, a centrifuge machine (not shown), a highly concentrated first component 4' with other constituents are obtained from the first component 4 in the first room 122. In other embodiments, the control module 16 can be further operated to conduct the tubes 162, 166 for the highly concentrated first component 4' to be output to outside the container body 12.

The present invention is disclosed by the preferred embodiments in the aforementioned description; however, it is contemplated for one skilled at the art that the embodiments are applied only for an illustration of the present invention rather than are interpreted as a limitation for the scope of the present invention. It should be noted that the various substantial alternation or replacement equivalent to these embodiments shall be considered as being covered within the scope of the present invention. Therefore, the protection scope of the present invention shall be defined by the claims.

What is claimed is:

1. A liquids separation kit that simultaneously holds a first component and a second component separated from a liquid after separation process, the liquids separation kit comprising:

a container body including a first room and a second room, both having a free end and a connecting end, wherein the first room holds said liquid or said first component and the second room holds said second component;

a connecting piece having a first end and a second end, said first end connecting to said connecting end of said first room, wherein a portion of the connecting piece is located in a space between said first and second rooms, or wherein a portion of the connecting piece is arranged outside said second room and the second end thereof is extending towards the free end of said second room, or wherein the connecting piece is arranged inside said second room and has the second end thereof extending towards the free end of said second room, rendering said second end thereof being arranged inside said second room;

a control module including a plurality of tubes and a control unit, said control unit coupled to said tubes for conducting or stopping liquids flows within said tubes by operating said control unit, said plurality of tubes being respectively connected to said second end, said second room, and said free end of said second room; and a piston disposed in said first room, said piston being movable within said first room to produce a suction force or a pressing force at said connecting end of said first room.

2. The liquids separation kit defined in claim 1 further includes a top cap arranged at the free end of the first room for confining the piston to being inside the first room.

3. The liquids separation kit defined in claim 1, wherein the control unit is operated and enables the second end and the free end of the second room to be in fluid communication with each other, thereby said liquid is sucked into the first room from the free end of the second room when the piston is moving from the connecting end of the first room towards the free end of the first room.

4. The liquids separation kit defined in claim 1, wherein the control unit is operated and enables the second end and the second room to be in fluid communication with each other, thereby the second component is pushed into the second room from the first room when the piston is moving from the free end of the first room towards the connecting end of the first room.

5. The liquids separation kit defined in claim 1, wherein the control unit is operated and enables the second end and the free end of the second room to be in fluid communication with each other, thereby the first component is pushed to the free end of the second room from the first room when the piston is moving from the free end of the first room towards the connecting end of the first room.

6. The liquids separation kit defined in claim 3, wherein the piston moves via pulling and pressing of an external force to change its position within the first room.

7. The liquids separation kit defined in claim 3 further includes a threaded rod connecting to the piston and driven by the external force to change the position of the piston within the first room.

8. The liquids separation kit defined in claim 1 further includes a bottom cap engaging the free end of the second room, in order to prevent the free end of the second room from being connecting to outside the container body.

9. The liquids separation kit defined in claim 1, further comprising an observation section disposed between the connecting piece and an inner periphery of the second room, wherein the observation section is transparent and formed by at least one of a block, a blocking element and a protruding element to expose the connecting piece for observation of at least one of the liquid in the connecting piece, the first component and the second component.

10. The liquids separation kit defined in claim 4, wherein the piston moves via pushing and pressing of an external force to change its position within the first room.

11. The liquids separation kit defined in claim 5, wherein the piston moves via pushing and pressing of an external force to change its position within the first room.

12. The liquids separation kit defined in claim 4 further includes a threaded rod connecting to the piston and driven by the external force to change the position of the piston within the first room.

13. The liquids separation kit defined in claim 5 further includes a threaded rod connecting to the piston and driven by the external force to change the position of the piston within the first room.

* * * * *